(12) United States Patent
Charlton et al.

(10) Patent No.: US 7,549,323 B2
(45) Date of Patent: Jun. 23, 2009

(54) DIAGNOSTIC TEST STRIP FOR COLLECTING AND DETECTING AN ANALYTE IN A FLUID SAMPLE AND METHOD FOR USING THE SAME

(75) Inventors: Steven C. Charlton, Osceola, IN (US); Karen L. Marfurt, Mishawaka, IN (US); Sung-Kwon Jung, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 285 days.

(21) Appl. No.: 11/579,720

(22) PCT Filed: May 13, 2005

(86) PCT No.: PCT/US2005/016774

§ 371 (c)(1),
(2), (4) Date: Nov. 3, 2006

(87) PCT Pub. No.: WO2005/112742

PCT Pub. Date: Dec. 1, 2005

(65) Prior Publication Data

US 2007/0275476 A1    Nov. 29, 2007

Related U.S. Application Data

(60) Provisional application No. 60/571,392, filed on May 14, 2004.

(51) Int. Cl.
G01N 31/22 (2006.01)
G01N 33/49 (2006.01)
G01N 21/00 (2006.01)

(52) U.S. Cl. .......................... 73/53.01; 422/55; 422/56; 422/58; 422/68.1; 422/82.05; 422/82.09; 436/46; 436/169; 436/170

(58) Field of Classification Search ............. 422/56–58, 422/68.1, 82.05, 82.09; 436/46, 164, 169, 436/170; 73/53.01
See application file for complete search history.

(56) References Cited

U.S. PATENT DOCUMENTS

| | | | |
|---|---|---|---|
| 5,279,294 A | 1/1994 | Anderson et al. | |
| 5,747,351 A | 5/1998 | Hemmati | 436/514 |
| 5,916,156 A | 6/1999 | Hildenbrand et al. | |
| 6,326,214 B1 * | 12/2001 | Liu et al. | 436/518 |
| 6,531,040 B2 | 3/2003 | Musho et al. | |

(Continued)

OTHER PUBLICATIONS

Written Opinion corresponding to International Patent Application No. PCT/US2005/016774, European Patent Office, dated Jan. 24, 2006, 11 pages.

(Continued)

*Primary Examiner*—Daniel S Larkin
(74) *Attorney, Agent, or Firm*—Nixon Peabody LLP

(57) ABSTRACT

A system and method for determining the concentration of an analyte in a fluid sample includes a test strip having a first and second portion separated by a bend line formed in the base. The bend line traverses the longitudinal axis of the base and the base is adapted to bend about the bend line. The test strip further includes a test element disposed on one of the portions. The test strip includes a reagent adapted to react with the analyte in the fluid sample.

30 Claims, 15 Drawing Sheets

U.S. PATENT DOCUMENTS

| | | |
|---|---|---|
| 6,582,964 B1 | 6/2003 | Samsoondar et al. .......... 436/67 |
| 2002/0192807 A1 | 12/2002 | Haviland et al. ......... 435/287.2 |
| 2003/0073152 A1 | 4/2003 | Phillips et al. |
| 2003/0175993 A1 | 9/2003 | Toranto et al. .............. 436/518 |

OTHER PUBLICATIONS

International Search Report corresponding to International Patent Application No. PCT/US2005/016774, European Patent Office, dated Jan. 24, 2006, 7 pages.

* cited by examiner

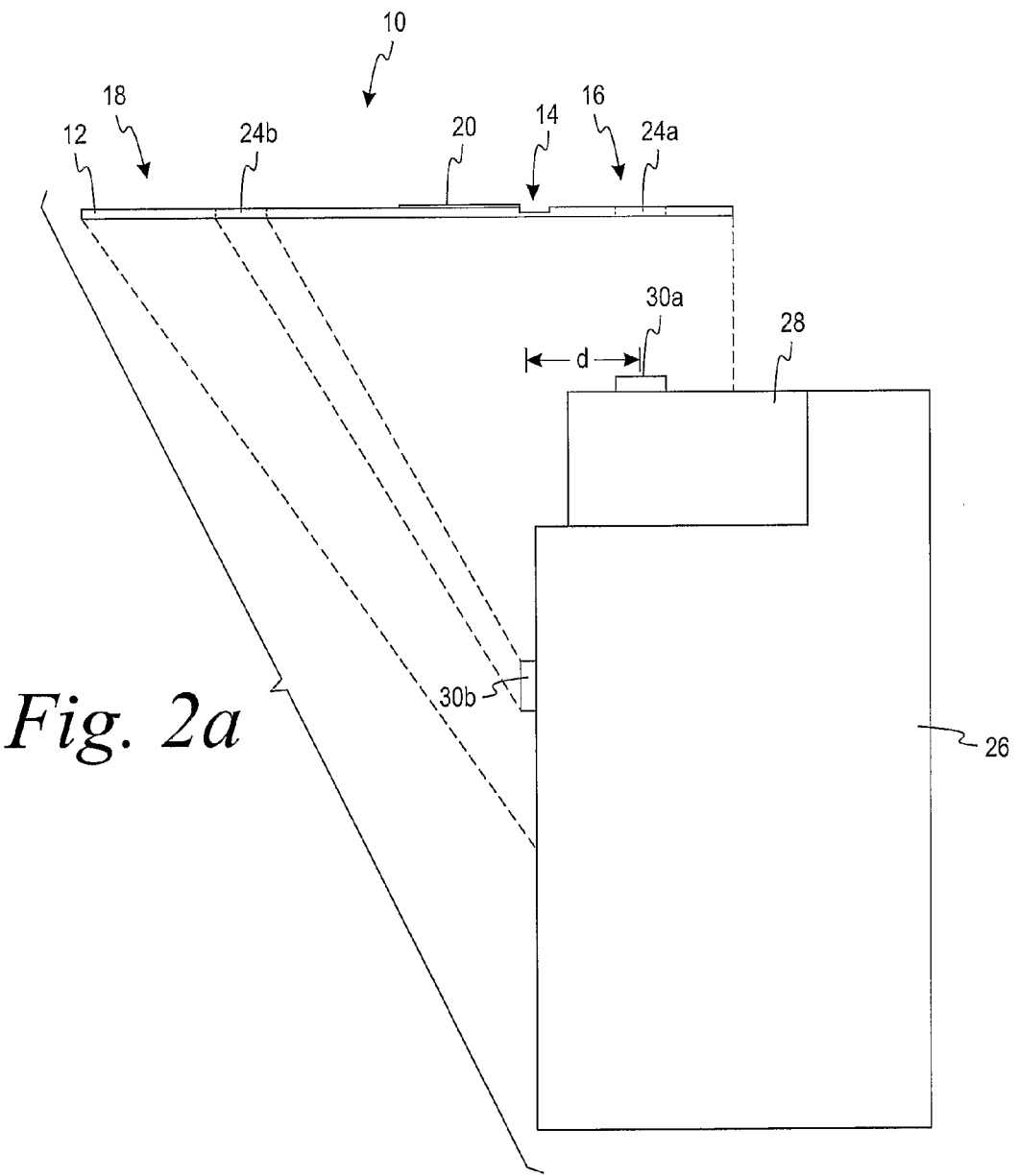

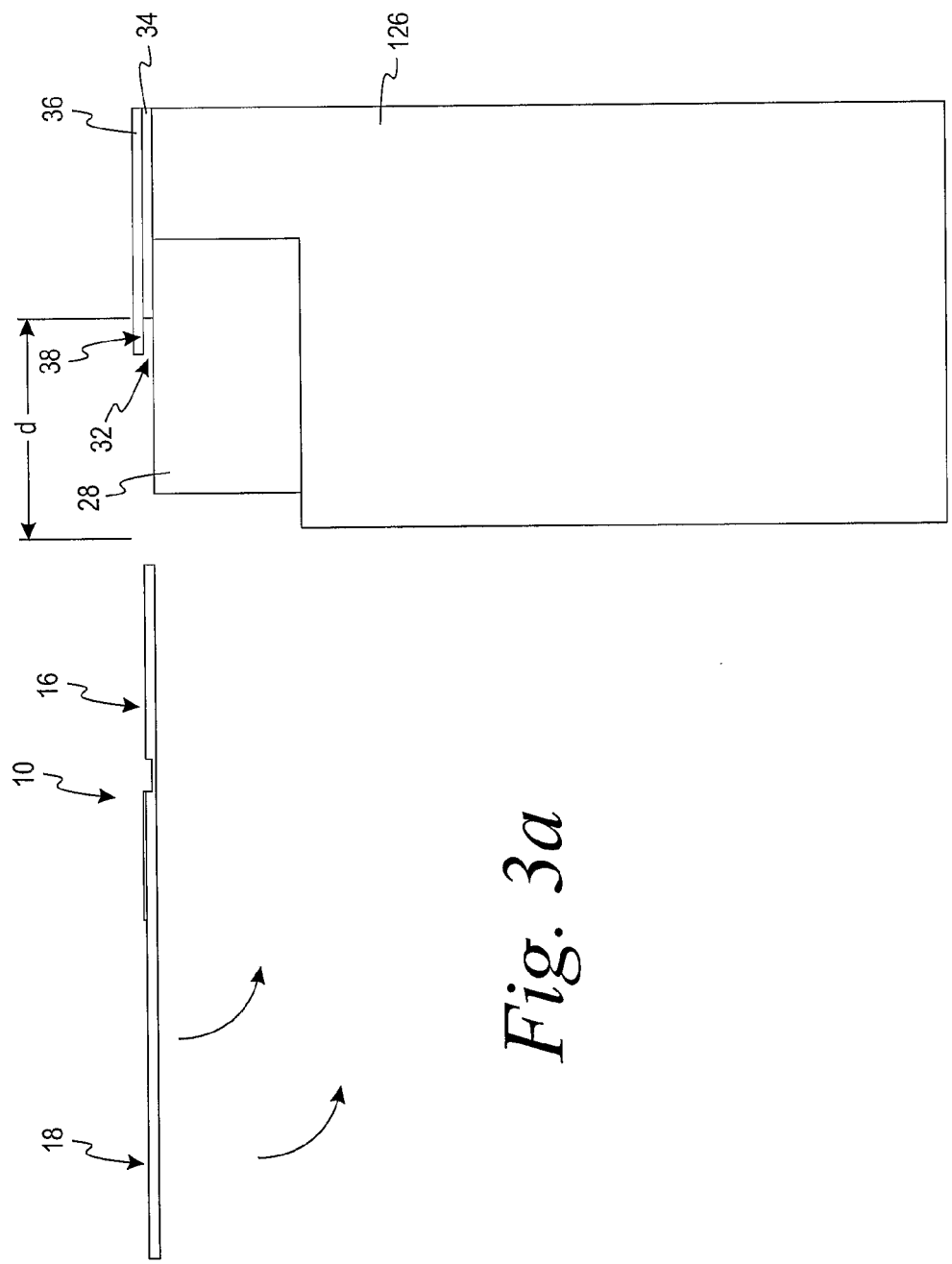

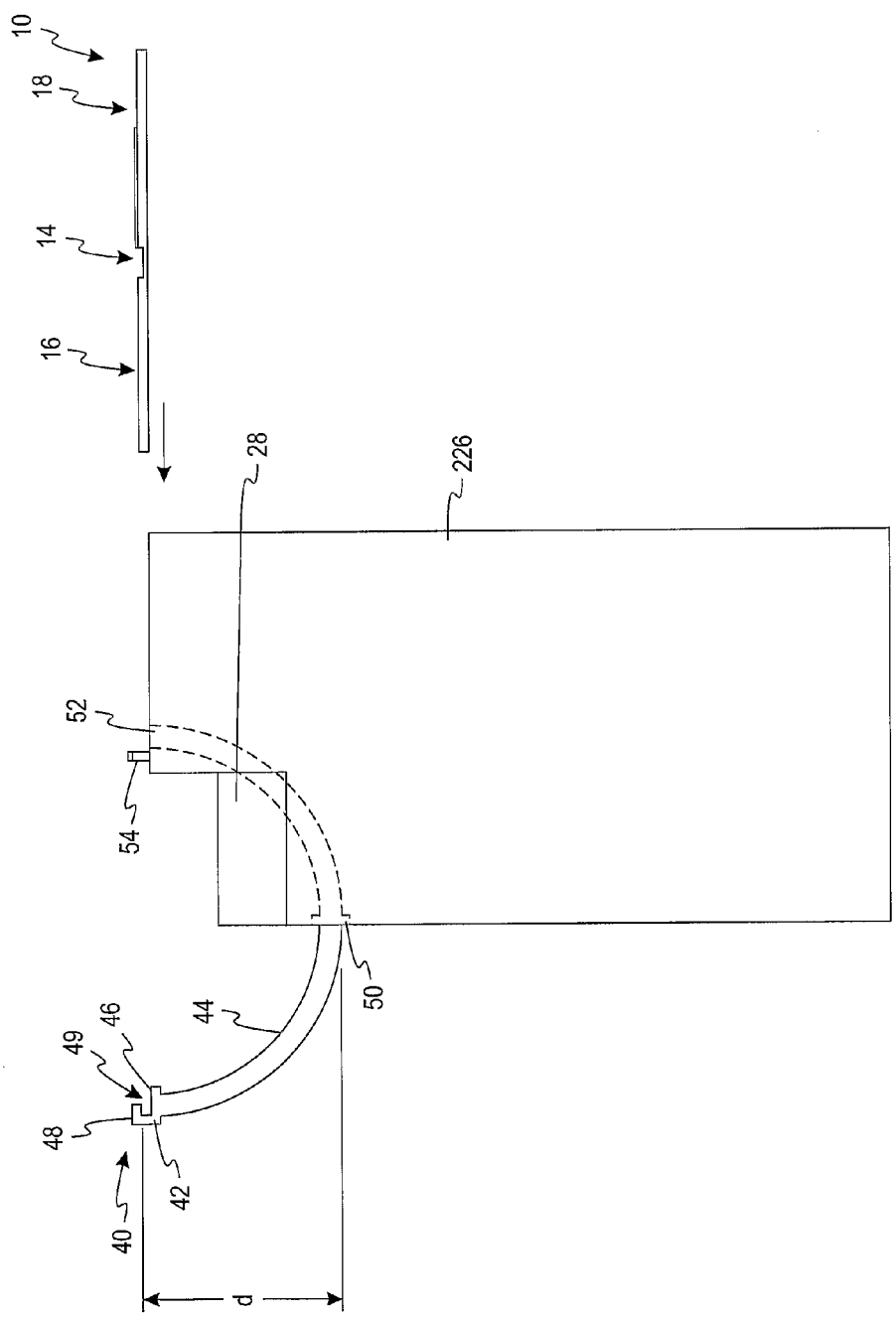

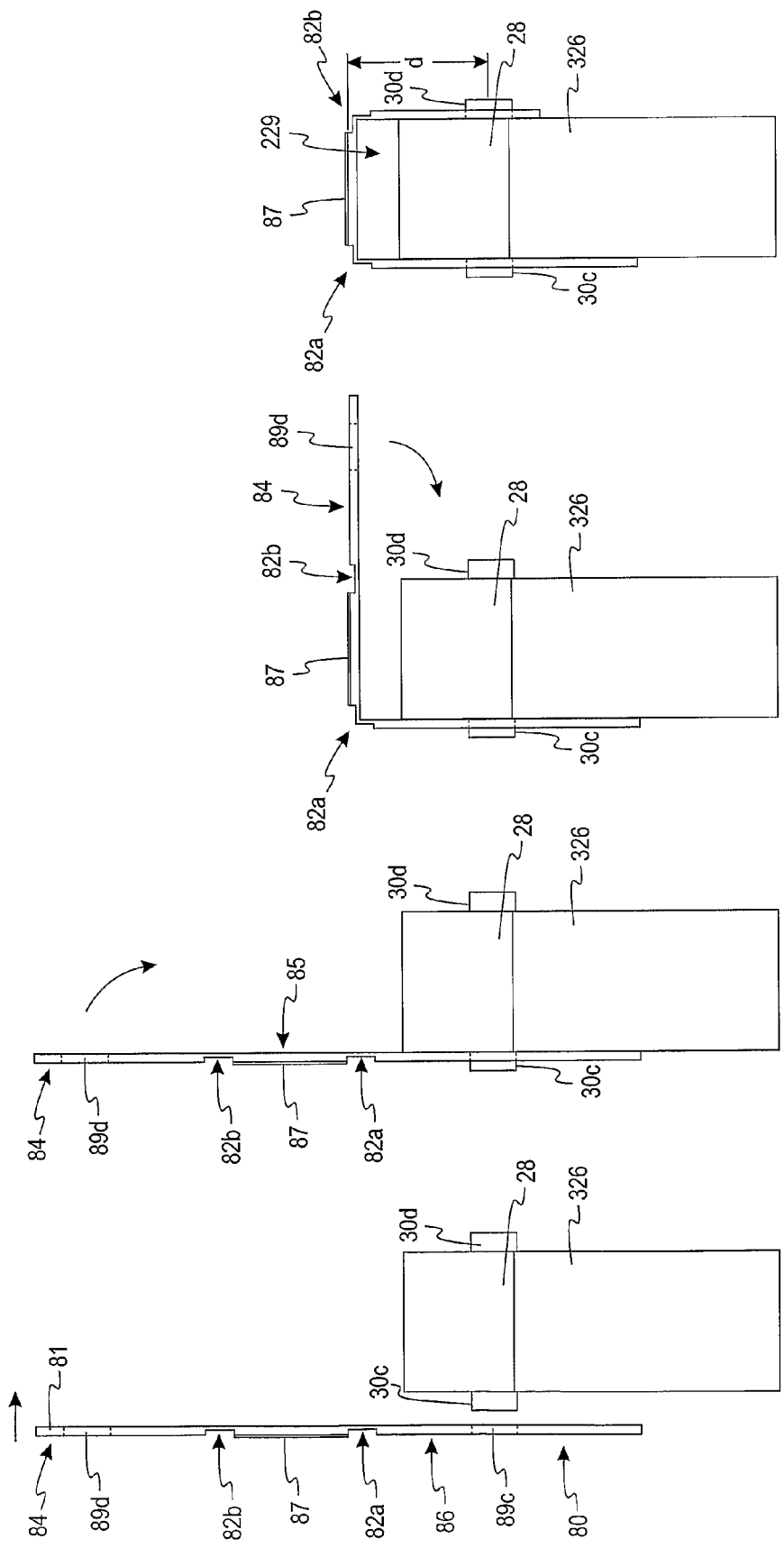

DIAGNOSTIC TEST STRIP FOR COLLECTING AND DETECTING AN ANALYTE IN A FLUID SAMPLE AND METHOD FOR USING THE SAME

CROSS-REFERENCE TO RELATED APPLICATIONS

This application is a U.S. national stage of International Application No. PCT/US2005/016774, filed May 13, 2005, which is related to and claims the benefit of U.S. Provisional Application No. 60/571,392, filed May 14, 2004, which is incorporated by reference in its entirety.

FIELD OF THE INVENTION

The present invention relates generally to diagnostic instruments and, more particularly, to a diagnostic test strip for use in determining the concentration of an analyte in a liquid sample.

BACKGROUND OF THE INVENTION

Test strips (e.g., biosensors) containing reagents are often used in assays for determining the concentration of an analyte in a fluid sample. Testing and self-testing for the concentration of glucose in blood is a common use for test strips. One method of obtaining a blood sample and analyzing the sample to determine the glucose level is with a lancing device and a separate blood collection device. In obtaining a blood sample, a drop of blood is obtained from the fingertip using the lancing device, and the blood is harvested using a test strip, which is then analyzed by a test unit that determines the concentration of glucose in the blood. Test strips may also used for determining the concentration or presence of various other analytes (e.g., fructosamine, hemoglobin, cholesterol, glucose, alcohol, drugs including illegal drugs, etc.) in a variety of body fluids (e.g., blood, interstitial fluid, saliva, urine, etc.). In use, a blood sample is harvested by a test strip and inserted into a meter. An optical read-head contained in the meter is used to optically determine the presence and concentration of an analyte in the sample. The test strip is typically placed into direct contact with the optical read-head or surrounding structures. The close proximity of the test strip to the read head or surrounding structures can allow the sample to contaminate these components. It is desirable to protect the read-head from contact with the sample to prevent contamination and ensure an accurate reading.

SUMMARY OF THE INVENTION

A system for determining the concentration of an analyte in a fluid sample according to one embodiment of the present invention is disclosed. The system includes a test strip having a first and second portion separated by a bend line formed in the base. The bend line traverses the longitudinal axis of the base and the base is adapted to bend about the bend line. The test strip further includes a test element disposed on one of the portions. The test strip includes a reagent adapted to react with the analyte in the fluid sample. The system further includes a meter which includes a read-head for analyzing the reaction and a receiving area adapted to receive the first portion of the base of the test strip. The receiving area of the meter receives the first portion of the base of the test strip, where the test strip is adapted to be bent about the bend line such that the second portion of the test strip is disposed over the read-head. The first portion of the test strip positions the second portion of the test strip a predetermined distance from the read-head such that a spacing is created between the second portion of the test strip having the test element disposed thereon and the read-head.

A method for determining the concentration of an analyte in a fluid sample according to another embodiment of the invention is disclosed. The method includes the acts of providing a test strip which includes a base having a first portion and a second portion separated by a bend line formed in the base. The bend line traverses the longitudinal axis of the base and the base is adapted to bend about the bend line. The test strip further includes a test element including a reagent disposed on the one portion of the base. The method further includes providing a meter that includes a read-head for analyzing the reaction and a receiving area adapted to receive the first portion of the base. The method also includes receiving the first portion of the test strip in the receiving area and bending the test strip at the bend line to create a spacing between the read-head and the test element. The first receiving area is used to position the second portion of the bent test strip a predetermined distance from the read head.

A test strip for use in the determination of an analyte in a fluid sample according to another embodiment of the present invention is disclosed. The test strip includes a base having a first portion and a second portion separated by a bend line formed in the base. The bend line traverses the longitudinal axis of the base and the base is adapted to bend about the bend line. The test strip further includes a test element disposed on the base proximate the bend line.

The above summary of the present invention is not intended to represent each embodiment, or every aspect, of the present invention. Additional features and benefits of the present invention are apparent from the detailed description, figures, and claims set forth below.

BRIEF DESCRIPTION OF THE DRAWINGS

FIG. 2a is a side view of the test strip of FIG. 1, and meter for reading the test strip according to one embodiment of the present invention.

FIG. 2b is a side view of the test strip of FIG. 1 after being disposed on the meter of FIG. 2a.

FIG. 3a is a side view of a test strip prior to being pocketed and disposed on a meter according to one embodiment of the present invention.

FIG. 3b is a side view of the test strip after being pocketed and disposed on the meter of FIG. 3a.

FIG. 4a is a side view of a test strip and meter, which is adapted to bend the test strip into an angled position, according to one embodiment of the present invention.

FIG. 4b is a perspective view of the meter of FIG. 4a.

FIG. 9a is a side view of the test strip of FIG. 8 prior to being disposed on a meter, according to one embodiment of the present invention.

FIG. 9b is a side view of the test strip of FIG. 8 partially disposed on the meter of FIG. 9a.

FIG. 9c is a side view of the test strip of FIG. 8 partially disposed on the meter of FIG. 9a after being bent once.

FIG. 9d is a side view of the test strip of FIG. 8 disposed on the meter of FIG. 9a after being bent twice.

Figure 1:
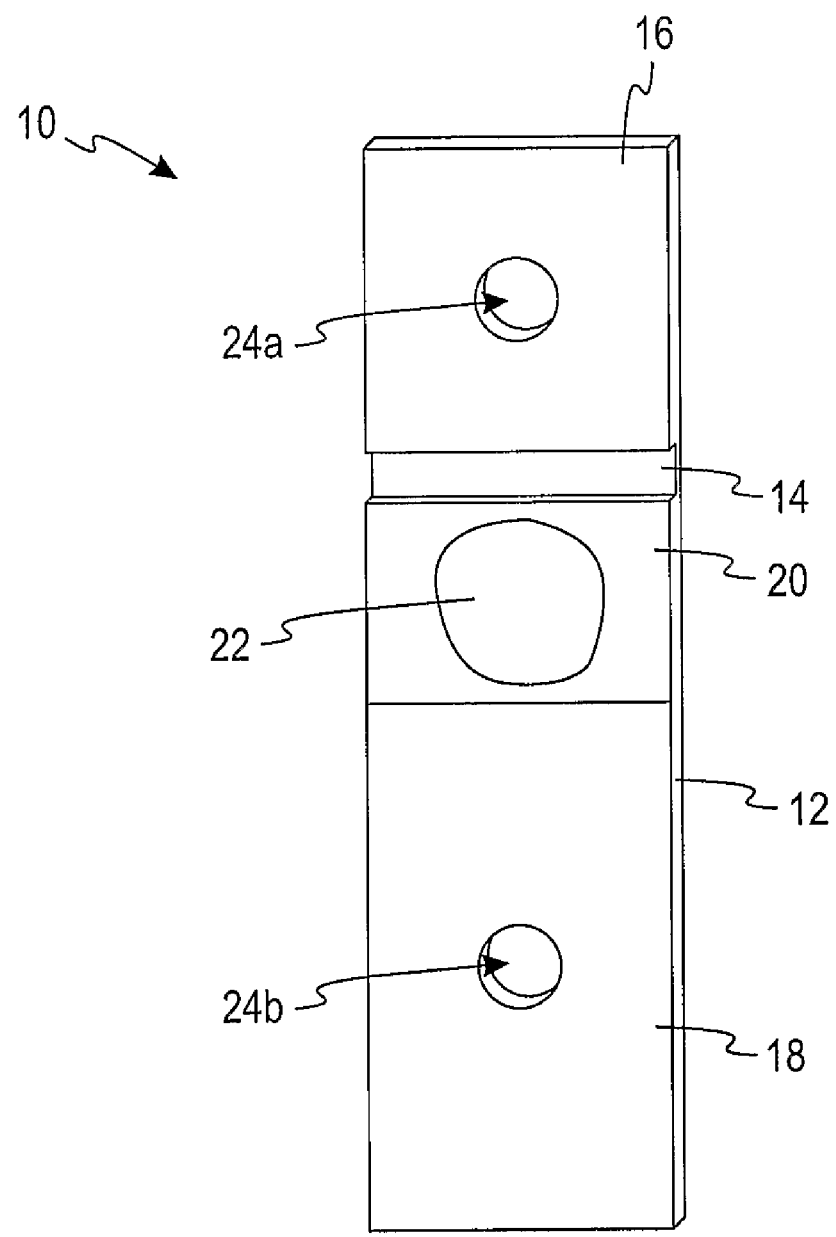
FIG. 1 is a perspective view of a top-fill test strip according to one embodiment of the present invention.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents and alternatives falling within the spirit and scope of the invention as defined by the appended claims.

DESCRIPTION OF ILLUSTRATED EMBODIMENTS

Turning now to the drawings and initially to FIG. 1, a test strip 10 is shown according to one embodiment of the present invention. The illustrated test strip 10 is referred to as a "top fill" type because the sample is applied directly to a test area as described below. The test strip 10 includes a base 12 having a bend line 14 that divides a tab end 16 of the test strip 10 from a main end 18. The bend line 14 comprises a substantially linear groove disposed at a substantially ninety degree angle with respect to the main axis of the base 12. A test element 20 is disposed on the base 12 and contains a reaction area 22 having one or more reagents for reacting with an analyte of interest in a fluid sample. A first alignment aperture 24a is located on the tab end 16 and a second alignment aperture 24b is located on the main end 18 of the base 12. In the illustrated embodiment, the alignment apertures 24a-b are cylindrical and extend through the base 12.

Figure 2B:
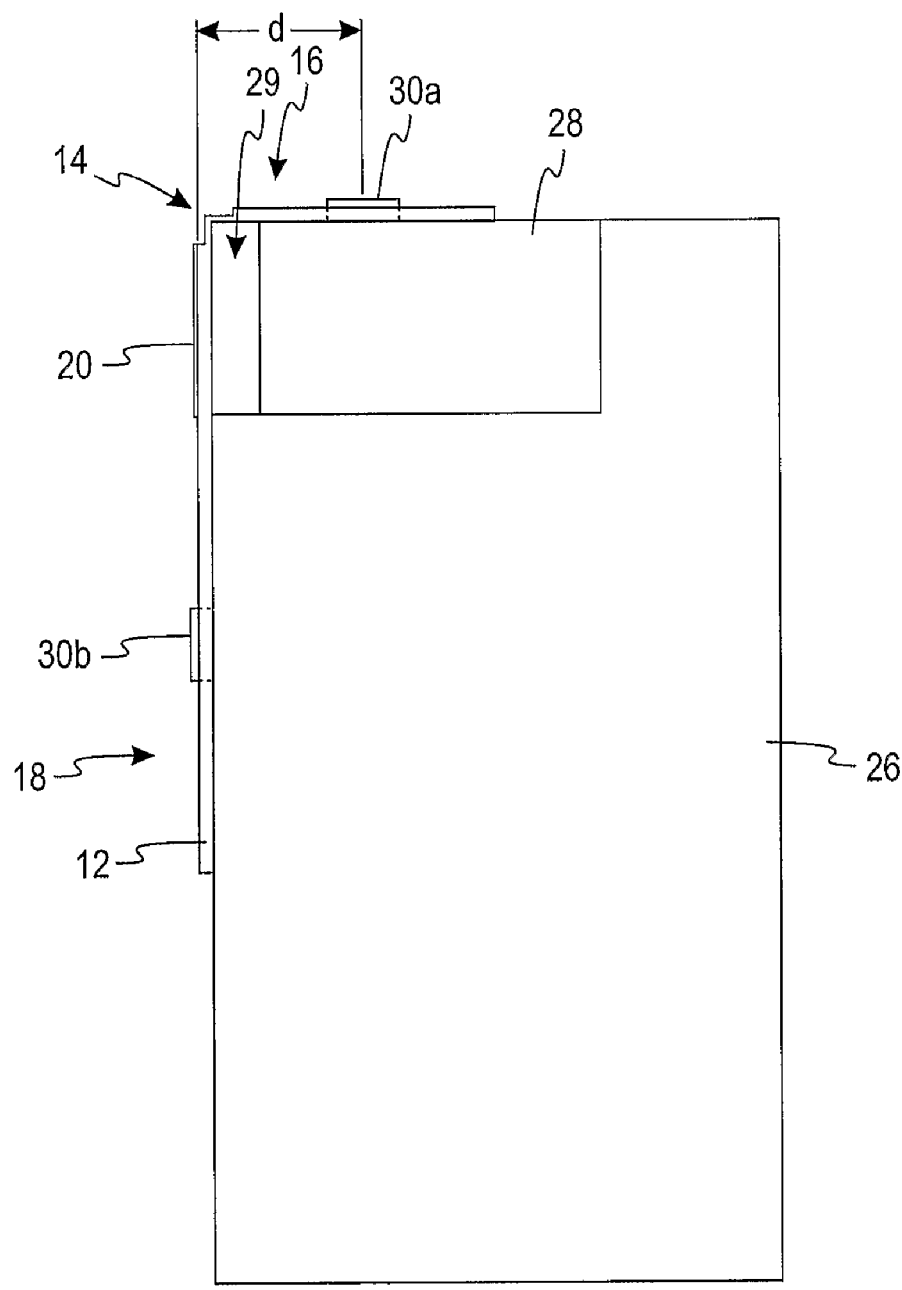

Referring also to FIGS. 2a and 2b, the test strip 10 is shown being disposed upon a meter 26 that includes an optical read-head 28. The meter 26 includes a first alignment pin 30a comprising a first receiving area and a second alignment pin 30b comprising a second receiving area. The use of the first alignment pin 30a creates a predetermined distance d between the alignment pin 30a and the test element 20. The base 12 of the test strip 10 is constructed of a substantially optically clear material to allow the optical read-head to analyze the reaction area 22 through the base 12. An example of such a material is polyethylene terephthalate (PET). In FIG. 2a, the test strip 10 is positioned so that the alignment aperture 24a is directly aligned with the alignment pin 30a that comprises the first receiving area of the meter 26. Once the test strip 10 is aligned, the test strip 10 is downwardly moved (as viewed in FIG. 2a) so as to insert the alignment pin 30a through the alignment aperture 24a. After the test strip 10 is substantially flush with the outer surface of the meter 26, the main end 18 of the base 12 is moved towards the meter's surface (i.e., downwardly rotated in FIG. 2a) so as to insert the alignment pin 30b that comprises the second receiving area through the alignment aperture 24b. This motion causes the base 12 to bend at the bend line 14, as shown in FIG. 2b.

Upon completion of the bending and after the alignment pins 30a-b have been inserted into the alignment apertures 24a-b, the test strip 10 is bent at an about 90 degree angle, and both the tab end 16 and the main end 18 are substantially flush with the outer surfaces of the meter 26. The bending of the test strip 10 creates a spacing 29 between the test element 20 and the read-head 28. The spacing 29 is predetermined by the first alignment pin 30a because a predetermined distance d is created between the test element 20 the first alignment pin 30a. Thus, the distance of the spacing 29 between the test element 20 and the read-head 28 is predetermined by placing the read-head 28 at a specific position relative to the first alignment pin 30a when designing the meter 26.

Once the spacing 29 has been created by bending the test strip 10, a sample may be directly applied to the test element 20 of the test sensor 10. The test element 20 remains a distance from the read-head 28 during the application and evaluation of the sample, which reduces the chances that the sample may contaminate the read-head 28 or surrounding area.

As described above, the test element 20 contains the reaction area 22 that includes a reagent or reagents for use in determining the analyte concentration in the sample. The specific reagent incorporated into the test element 20 is a function of the analyte of interest and the type of assay to be used for determining the concentration of the analyte.

In one embodiment of the present invention, for example, the reaction area could contain reagents adapted to the determination of glucose, such as the enzyme glucose oxidase in combination with indicators such as tetramethylbenzidine or dianisidine or 4-aminoantipyrine plus p-hydroxybenzenesulfonate in the presence of peroxidase. In another embodiment of the present invention, the enzyme glucose dehydrogenase could be used in combination with tetrazolium indicators such as p-iodonitrotetrazolium violet (INT), nitroblue tetrazolium (NBT) or tetranitroblue tetrazolium (TNBT), for example.

In yet another embodiment of the present invention where the analyte is cholesterol, the reagent area contains the enzymes cholesterol ester hydrolase and cholesterol oxidase plus indicators such as tetramethylbenzidine or dianisidine or 4-aminoantipyrine plus p-hydroxybenzenesulfonate in the presence of peroxidase.

In another embodiment of the present invention where the analytes are tryglycerides, the enzymes lipase, glycerokinase, glycerolphosphate dehydrogenase and diaphorase in combination with tetrazolium indicators such as p-iodonitrotetrazolium violet (INT), nitroblue tetrazolium (NBT) or tetranitroblue tetrazolium (TNBT) will produce a color indicative of the tryglyceride levels. In yet another embodiment of the present invention, the enzymes lipase, glycerokinase, glycerol phosphate oxidase combined with indicators such as tetramethylbenzidine or dianisidine or 4-aminoantipyrine plus p-hydroxybenzenesulfonate in the presence of peroxidase will produce color in response to triglycerides.

According to another embodiment of the present invention, where the analyte is the enzyme amylase, the reagent area contains, for example, the enzyme alpha glucosidase and the chromogenic indicator 4,6-ethylidene (G7) nitrophenyl (G1)-(alpha)D-maltoheptoside. In another embodiment of the present invention, hemoglobin can be detected using, for example, potassium ferricyanide, potassium cyanide and sodium bicarbonate.

Upon applying the sample to the test element 20, the analyte reacts with the reagent(s) located in the reaction area 22 on the test element 20. The reaction is indicative of the analyte concentration in the sample and is evaluated using the read-head 28. In the illustrated embodiments, the width of the test element 20 is approximately the width of the test strip 10. In other embodiments, the width of the test element is less than the width of the test strip 10.

Figure 3B:
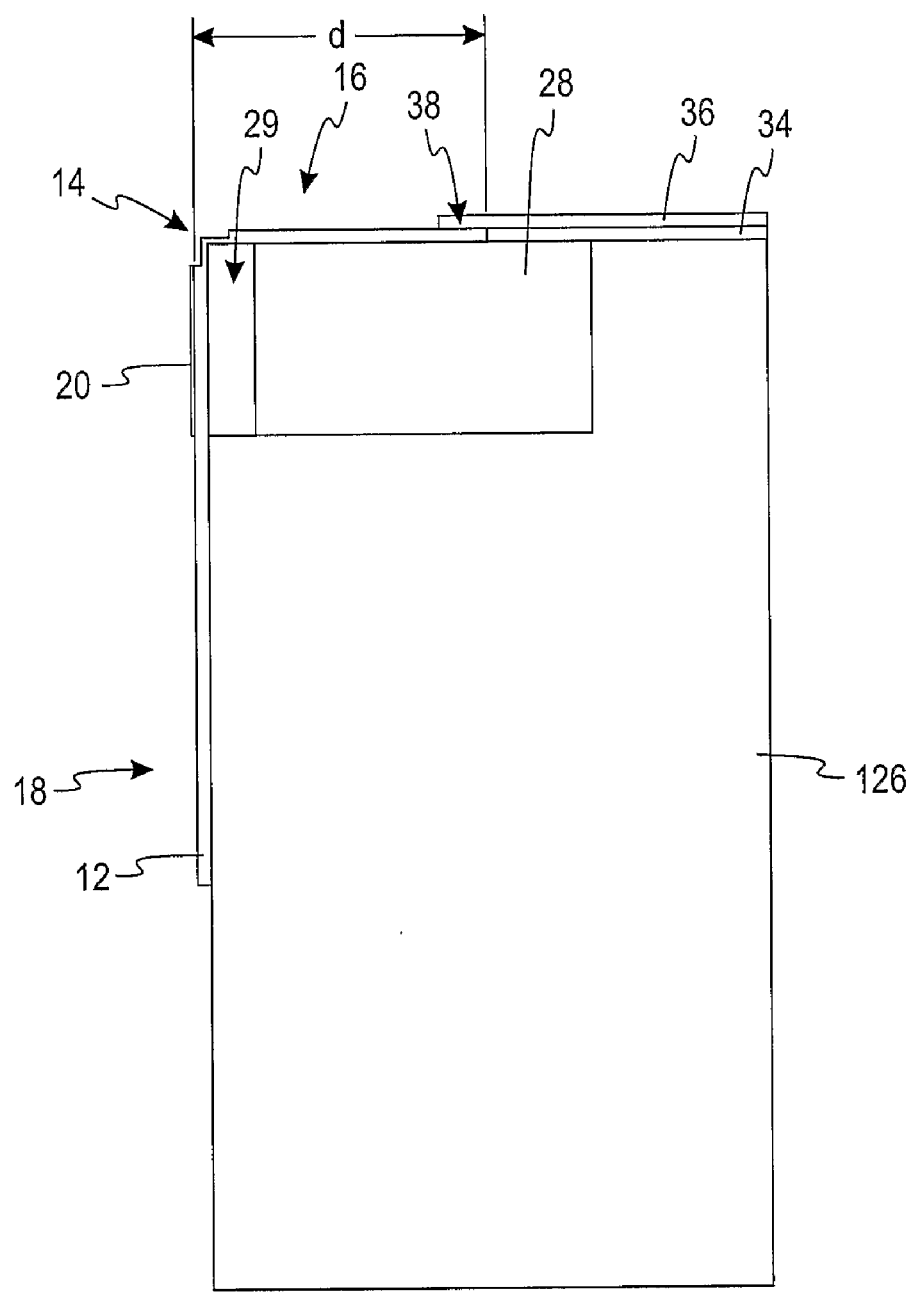

Referring to FIGS. 3a and 3b, a meter 126 is shown according to an alternative embodiment of the present invention. The meter 126 is adapted to allow a user to bend the test strip 10 by using a slot 32 that comprises a first receiving area of the meter 126. The slot 32 is formed from a spacer 34 located between the outer surface of the meter 126 and an upper plate 36. The upper plate 36 extends beyond the spacer 34 so as to create an overhang 38. The spacer 34 is at least the height of the test strip 10, thus, allowing the test strip 10 sufficient clearance to be inserted into the slot 32.

According to one embodiment of the present invention, the slot 32 is further equipped with side walls to help align the test strip 10 prior to bending. In this embodiment, a channel may be fashioned into the spacer so as to create the side walls. Alternatively, the side walls may be formed as extensions from the upper plate in the direction of the meter. In yet another embodiment, the slot 32 may be formed by using a single plate as opposed to a separate spacer and upper plate. In alternate embodiments, the slot may be located at any position on the meter so as to allow a test strip to be bent around the meter, thus protecting the read-head, and allowing the analyte of interest in the sample to be evaluated.

The tab end 16 of the test strip 10 is inserted into the slot 32 prior to being bent. As shown in FIG. 3b, the leading edge of the test strip 10 will abut the front edge of the spacer 34 and prevent the test strip 10 from being overly inserted into the slot 32. After placing the test strip 10 within the slot 32, a user applies pressure to the main end 18 to bend the test strip 10 at the bend line 14. Upon applying pressure to the main end 18, the tab end 16 of the test strip 10 is held in place within the slot 32 and the tab end 16 will remain flush with the outer surface of the meter 126. The positioning of the test strip 10 by the slot 32 creates a spacing 29 between the test element 20 and the read-head 28. The spacing 29 is predetermined by the slot 32 because a predetermined distance d is created between the test element 20 and the slot 32.

In one embodiment of the meter 126 having the slot 32, the meter 126 contains an alignment pin that comprises a second receiving area. The test strip 10 contains at least one alignment aperture similar to the alignment pin 30b and alignment aperture 24b shown in FIG. 2a. In other embodiments, the test strip 10 does not contain an alignment aperture. Additionally, in some embodiments of the meter 126, side walls of the slot 32 may aid in the alignment of the test strip 10.

Referring now to FIG. 4a, a meter 226 having a positioning device 40 for assisting a user with the bending of a test strip 10 is shown according to an alternative embodiment of the present invention. The positioning device 40 comprises a first receiving area and comprises a head 42 located at the distal end of an arm 44. The head 42 contains a platform 46 as its lower boundary and a lip 48 located above and substantially parallel to the platform 46. The lower surface of the lip 48 and the upper surface of the platform 46 define a moveable slot 49. Additionally, side walls may extend between the lip 48 and the platform 46 to prevent the transverse movement of the test strip 10 when inserted in the slot 49. The meter 226 also contains a channel 52 for receiving the arm 44 and an inlet 50 adapted to receive the platform 46 of the head 42. The channel 52 and inlet 50 receive the arm 44 and platform 46 as the positioning device 40 is moved between a loading position and an operating position.

Figure 4B:
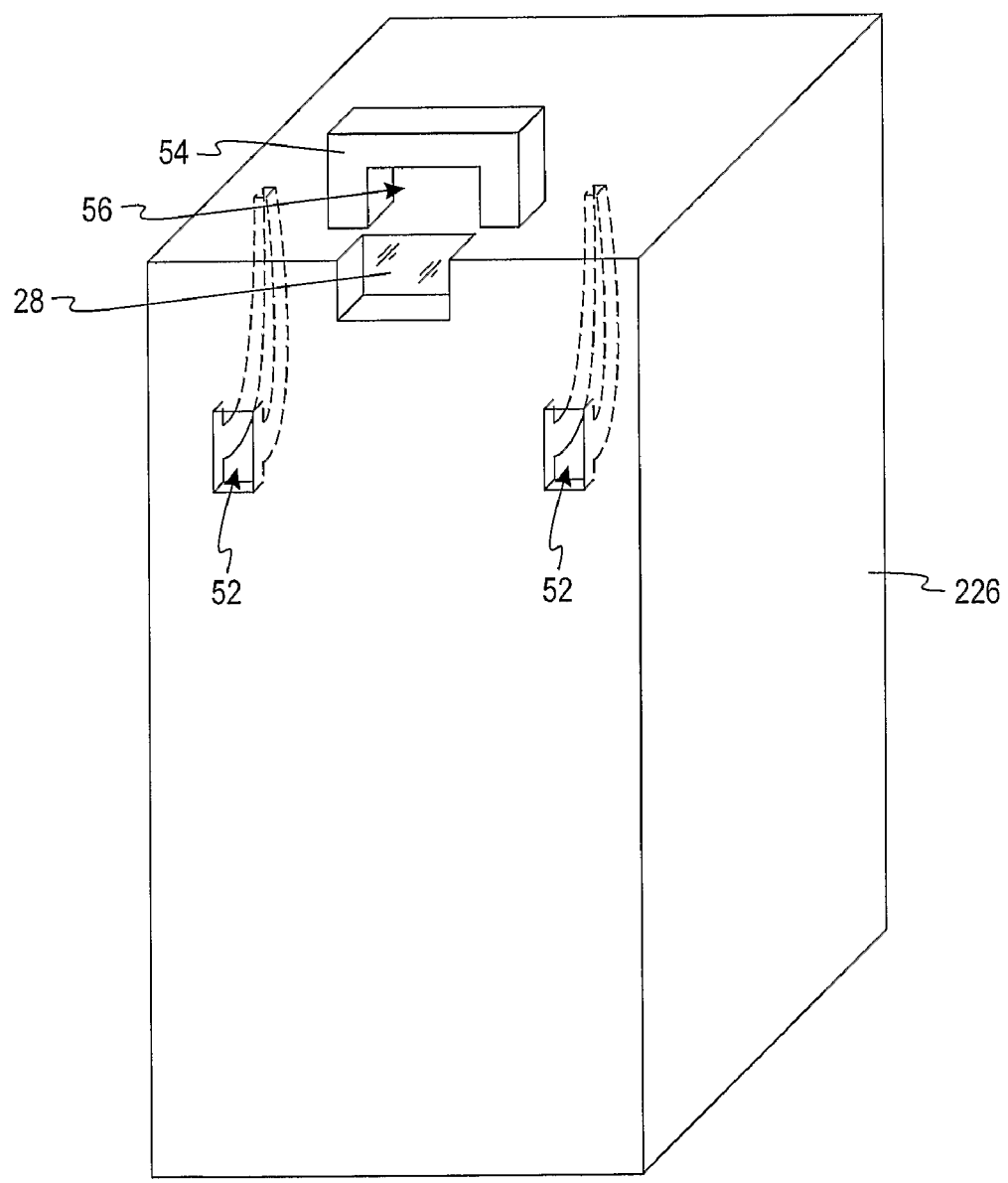

Referring also to FIG. 4b, a bridge 54 comprises a second receiving area on an upper surface of the meter 226. The bridge 54 is generally U-shaped and dimensioned to allow the test strip 10 to be inserted through an opening 56 of the bridge 54. In FIG. 4b, the positioning device 40 has been removed to better illustrate the bridge 54, the opening 56, the inlet 50, the channel 52, and the read-head 28. The embodiment in FIG. 4b illustrates the meter 226 as having two channels 52 from which two arms 44 may extend. However, it is contemplated by the inventors that a single opening is also sufficient to accomplish the positioning of the test strip.

Figure 4C:
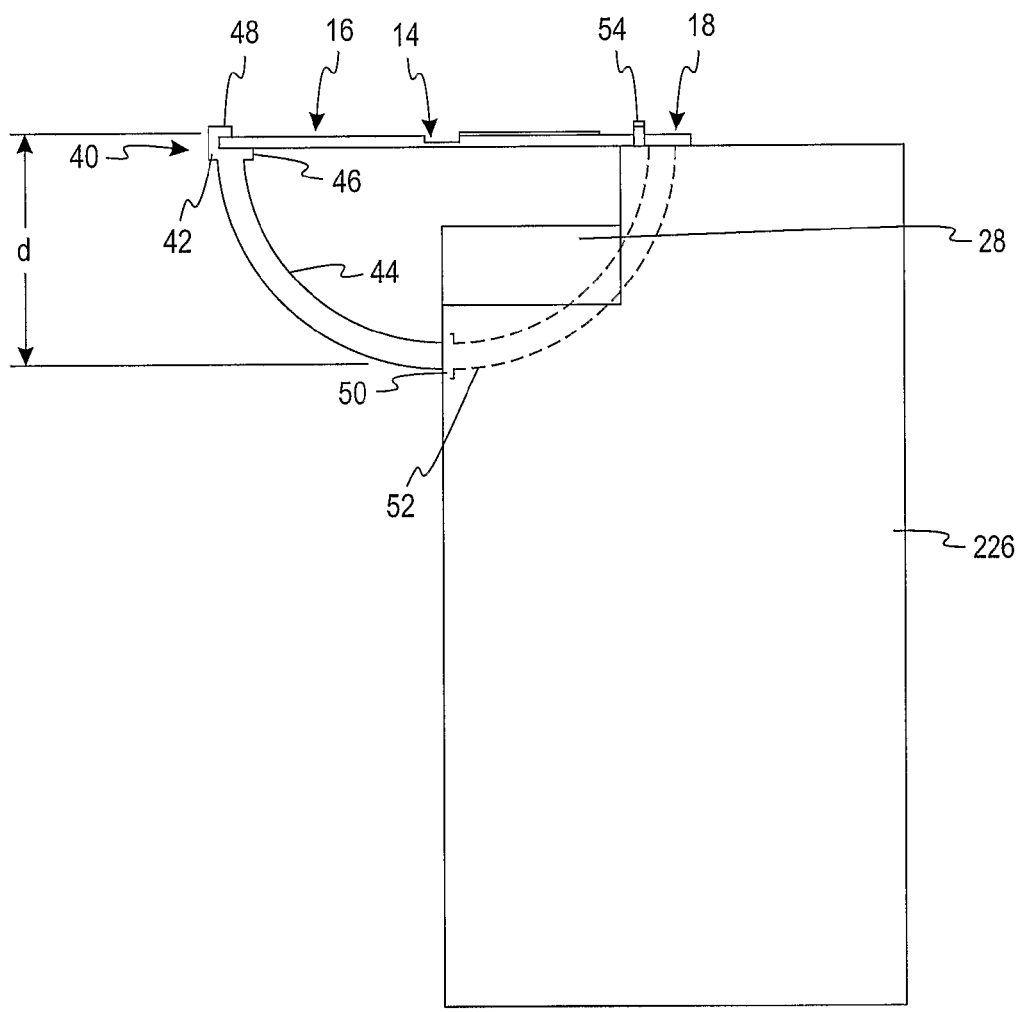
FIG. 4c is a side view of the test strip and meter of FIG. 4a upon insertion of the test strip.

Referring also to FIG. 4c, the positioning device 40 is shown in its loading position. In this position, the main end 18 of the test strip 10 is inserted through the opening 56 of the bridge 54 and into the slot 49 of the head 42 of the positioning device 40. When the test strip 10 is properly placed within the head 42, the lower surface of the test strip 10 is disposed on the upper surface of the platform 46 and the upper surface of the test strip 10 sits below the lip 48, thus, securing the test strip 10 within the moveable slot 49. Once the test strip 10 has been loaded as described above, a user may then actuate the positioning device 40 from its loading position to its operating position.

Figure 4D:
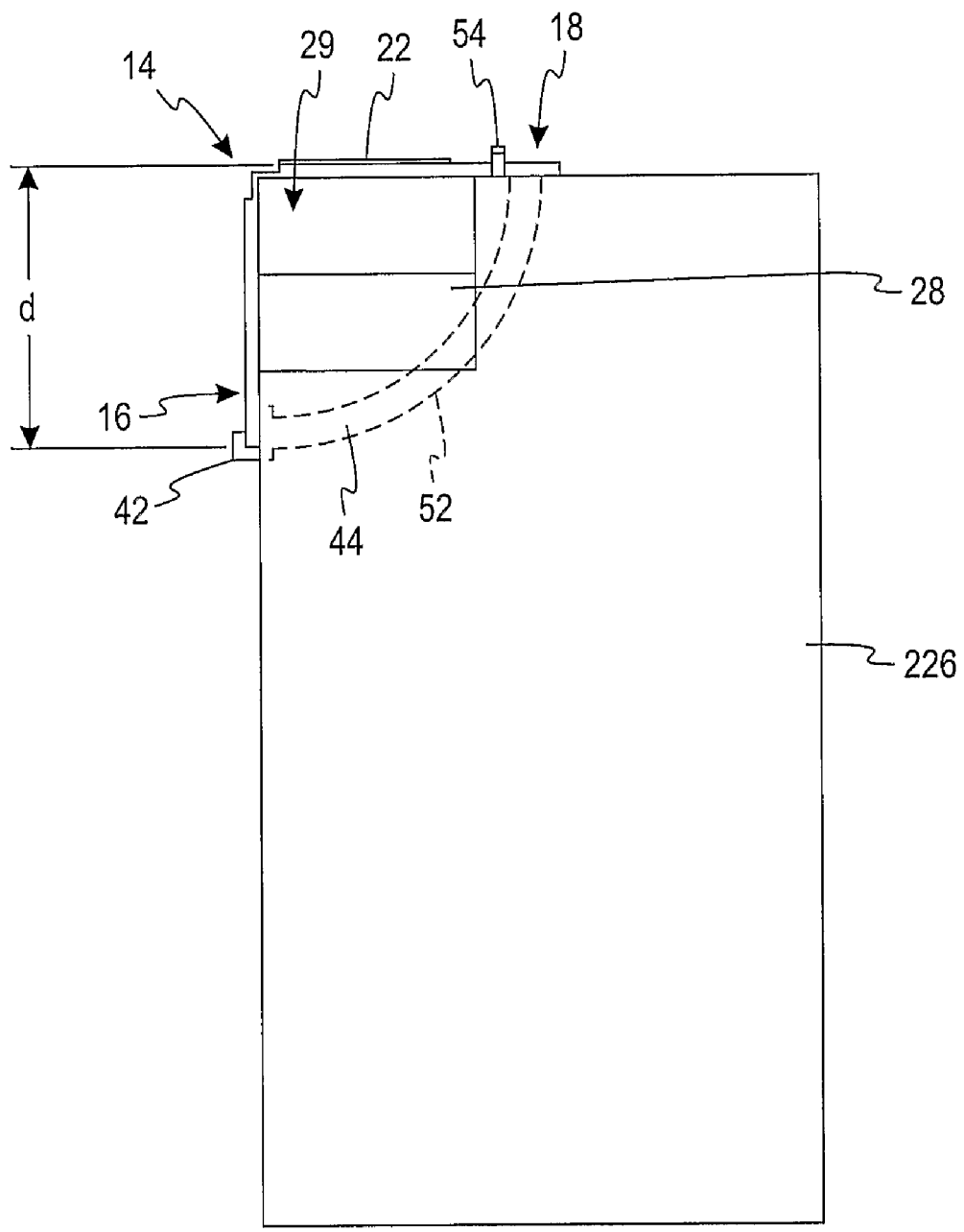
FIG. 4d is a side view of the test strip and meter of FIG. 4c after bending the test strip into its angled position.

In FIG. 4d, the positioning device 40 of the meter 226 is shown in its operating position. The arm 44 extends into the channel 52 as the positioning device passes through the inlet 50 and enters the channel. Upon reaching the inlet 50, the platform 46 of the head 42 extends into the inlet of the channel 52. When the positioning device 40 has been moved to the operating position, a spacing 29 is created between the test element 20 and the read-head 28. The spacing 29 is predetermined by the slot 49 because a predetermined distance d is created between the test element 20 the slot 49. In this position, the test strip 10 is disposed over and a distance from the read-head 28, thus reducing the chance of contamination of the read-head 28 when the sample is applied to the test element 20.

Figure 5:
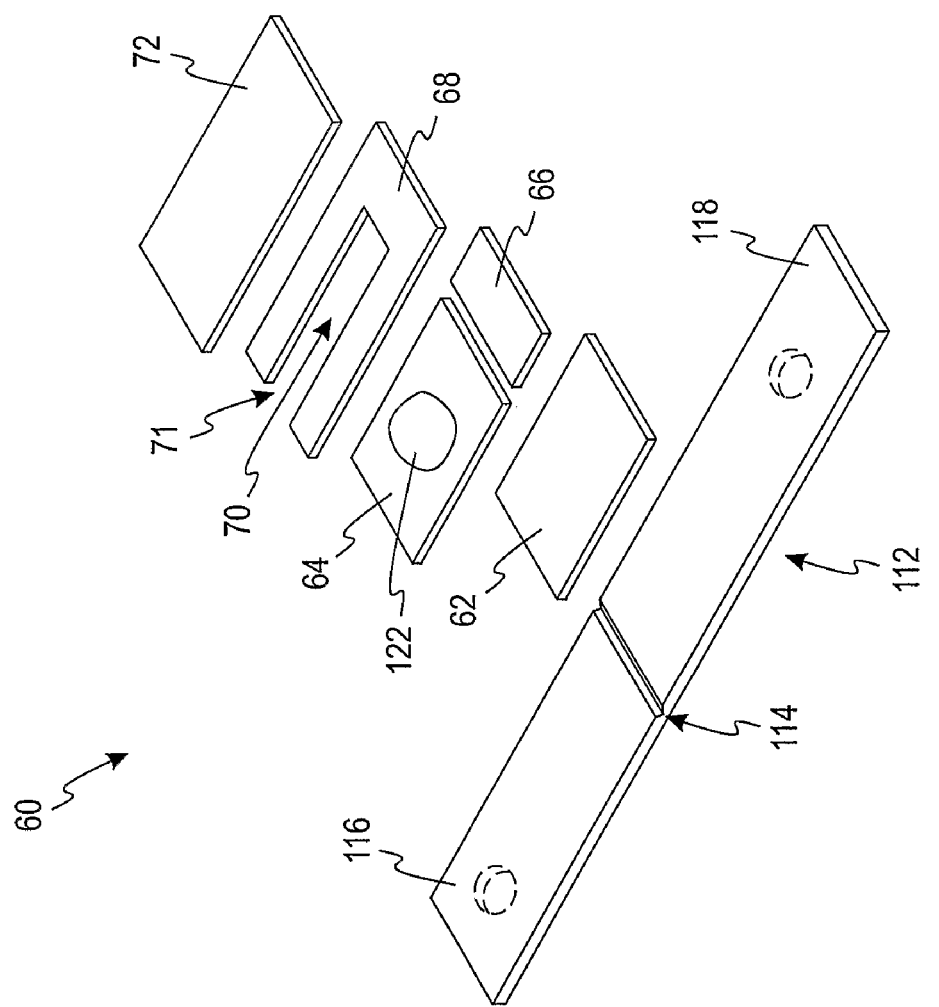
FIG. 5 is an exploded perspective view of a capillary fill test strip according to another embodiment of the present invention.

Referring now to FIG. 5, a capillary fill test strip 60 is shown according to another embodiment of the present invention. The test strip 60 comprises a base 112 containing a bend line 114 which separates a tab end 116 from a main end 118. A first double-sided adhesive layer 62 is applied to the main end 118 of the base 112. A test element 64 having a reagent 122 is positioned on the adhesive 62 opposite the base 112. An optional spacer 66 may be used to consume any additional room on the adhesive 62 not occupied by the test element 64 and for supporting additional layers. A second double-sided adhesive layer 68 is disposed over the test element 64 (and spacer 66 if present). The second adhesive 68 contains a capillary space 70 having an inlet 71. Finally, a lid 72 is disposed atop the second adhesive layer 68. The capillary channel of the test strip 60 is formed by the lower surface of the lid 72, the upper surface of the test element 64 (and spacer 66 if present), and the side walls of the capillary space 70. The capillary channel directs a fluid sample to the reagent 122 on the test element 62. In alternate embodiments, the test element 64 and first adhesive layer 62 are eliminated by depositing the reagent 122 directly on the base 112.

Figure 6:
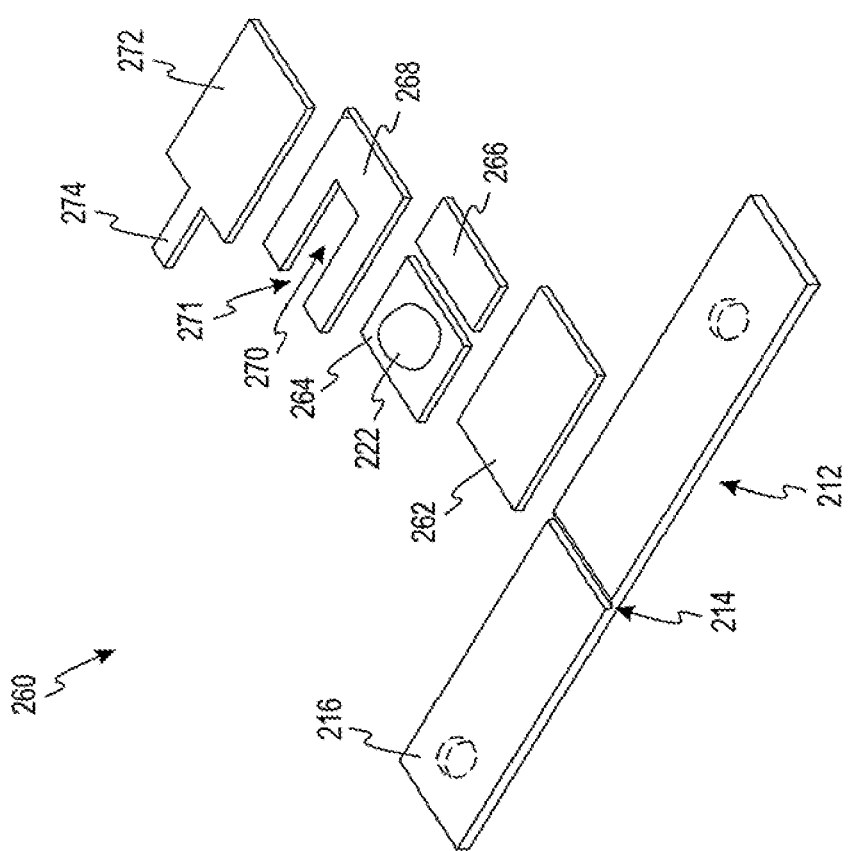
FIG. 6 is an exploded perspective view of a capillary fill test strip according to yet another embodiment of the present invention.

Turning now to FIG. 6, a capillary fill test strip 260 is shown according to another alternative embodiment of the present invention. In this embodiment, the test strip 260 is similar to the test strip 60 of FIG. 5, but includes a lip 274 that extends from the body of its lid 272. In the illustrated embodiment, the adhesive 262, the test element 264, the spacer 266, the adhesive 268 containing the capillary space 270, and the body of the lid 272 are approximately flush with the bend line 214 of the test strip 260. The lip 274 extends beyond the bend line 214 in the direction of the tab end 216 of the base 212. When the test strip 260 is positioned in a meter, the lip 274 aids in directing the sample into the inlet 271 of the capillary channel of the test strip 260.

In other alternative embodiments, the strips 60, 260 include an aperture in the lids 72, 272, respectively, for venting the capillary channels. Alternatively still, the lid 72, 272 and/or lip 274 is treated with a surfactant to aid in the transportation of the sample to the test element 64, 264. In yet other embodiments, the capillary fill test strips are provided with alignment apertures (illustrated in shadow in FIGS. 5 and 6) as discussed in connection with FIG. 1.

Figure 7:
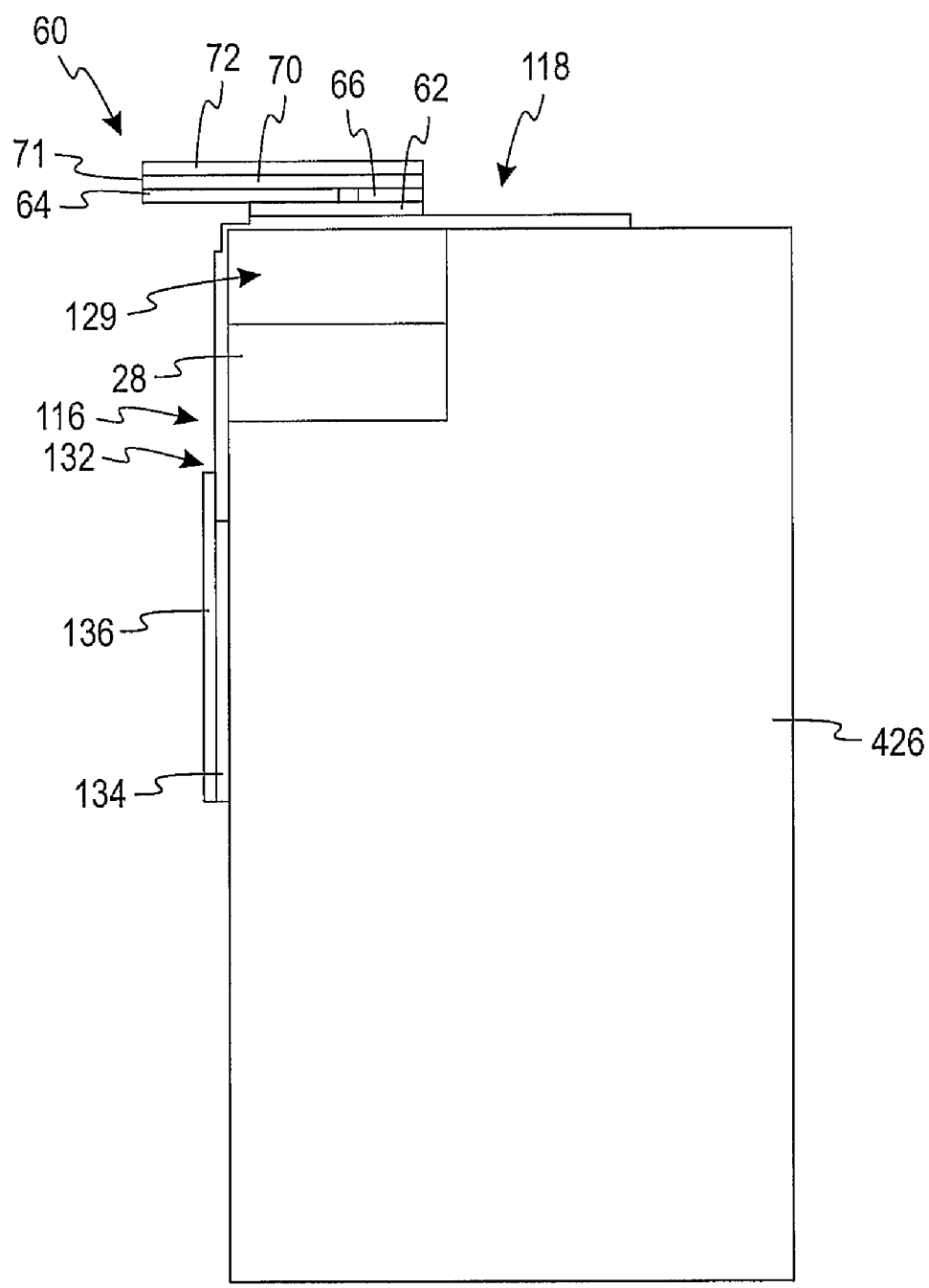
FIG. 7 is a side view of the capillary fill test strip of FIG. 5 after being disposed on a meter, according to one embodiment of the present invention.

Referring now to FIG. 7, the capillary fill test strip 60 of FIG. 5 is shown disposed on a meter 426 according to one embodiment of the present invention. In one embodiment, the meter 426 is equipped with a slot 132 that comprises a first receiving area. The slot 132 is similar to slot 32 describe above in connection with FIGS. 3a-b. In the embodiment shown in FIG. 7, the test element 64, adhesive 68, capillary space 70 (FIG. 5), and lid 72 extend beyond the plane of the tab end 116 of the folded test strip 60. Thus, the inlet 71 of the capillary channel is disposed externally from the meter 426 and the read-head 28 is protected by the folded test strip 60. Once the test strip 60 has been disposed on the meter 426, a user brings the capillary channel inlet 71 into contact with the sample. This embodiment further protects the read-head 28 by allowing sample collection to occur at a greater distance from the read-head 28.

Figure 8:
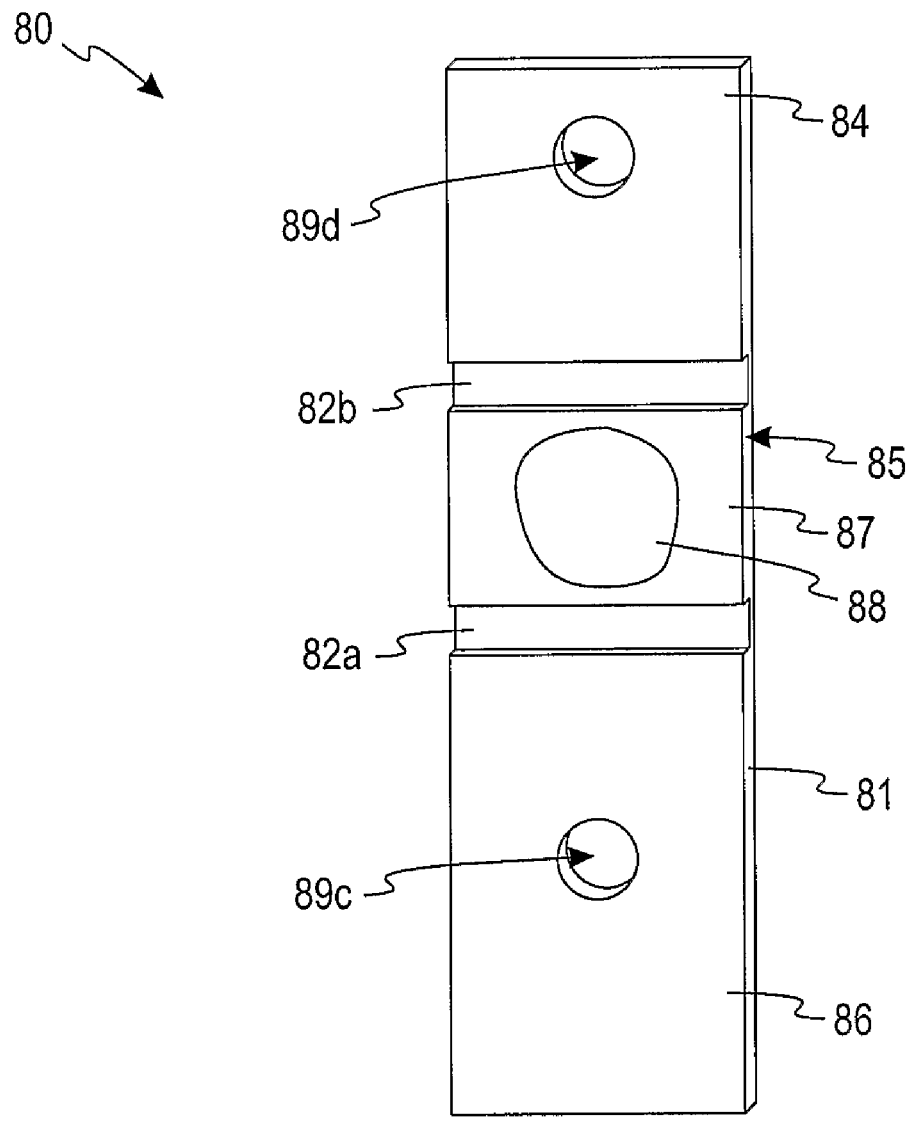
FIG. 8 is a perspective view of a top-fill test strip according to another embodiment of the present invention.

Referring now to FIG. 8, a top-fill test strip 80 is shown according to another alternative embodiment the present invention. The test strip 80 includes a base 81 partially separated by a first bend line 82a and a second bend line 82b into a tab end 84, a middle section 85, and a main end 86. Similar to the above-described test strips, the test strip 80 is adapted to bend about the first and second bend lines 82a,b. A test element 87 containing a reagent 88 is disposed on the middle section 85. An alignment aperture 89c is located on the main end 86 and another alignment aperture 89d is located on the tab end 84. In the illustrated embodiment, the alignment apertures are cylindrical and extend through the base 81.

Referring now to FIGS. 9a-d, the test strip 80 of FIG. 8 is shown being disposed upon a meter 326 that contains an optical read-head 28 for reading the test strip 80. The base 81 is constructed of a sufficiently optically clear material to allow the optical read-head 28 to analyze the sample. In FIG. 9a, the test strip 80 is positioned so that the alignment aperture 89c is aligned with the alignment pin 30c comprising a second receiving area. Once the test strip 80 is aligned, the test strip 80 is moved so as to insert the alignment pin 30c through the alignment aperture 89c, as shown in FIG. 9b.

Once the alignment pin 30c has been inserted, the tab end 84 and the middle section 85 is moved toward the read-head 28, as illustrated in FIG. 9c. The movement of the tab end 84 and the middle section 85 in this direction causes the base 81 to bend at the bend line 82a. From this position, the tab end 84 is moved so as to insert the alignment pin 30d comprises a first receiving area into the alignment aperture 89d, as can be seen in FIG. 9d. Upon inserting the alignment pin 30d, the test element 87 is substantially parallel to the read-head 28 and a spacing 229 is created between the test element 87 and the read-head 28. In one embodiment, the spacing 229 is predetermined by the alignment pins 30c-d because a predetermined distance d is created between the test element 87 and the alignment pins 30c,d. Thus, the distance of the spacing 229 between the test element 87 and the read-head 28 is predetermined by placing the read-head 28 at a specific position relative to the alignment pins 30c-d when designing the meter 326. Once a sample is applied to the test element 87, the reaction between the reagents and the sample can be analyzed. The use of the alignment pins 30c-d aids in maintaining the test strip 80 at the desired distance from the read-head 28 to guard against the sample contacting the read-head 28.

Figure 10A:
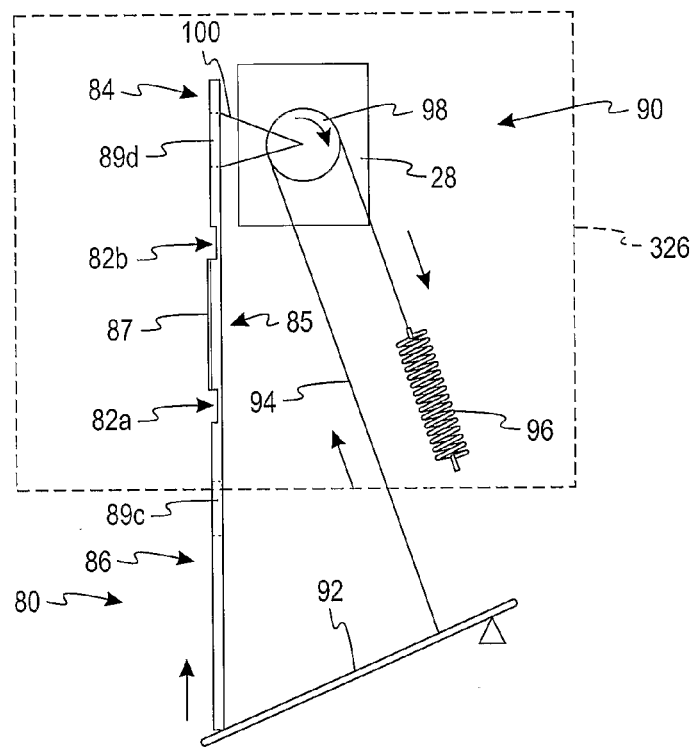
FIG. 10a is a side view of a meter and test strip positioning device prior to loading a test strip according to one embodiment of the present invention.
Figure 10B:
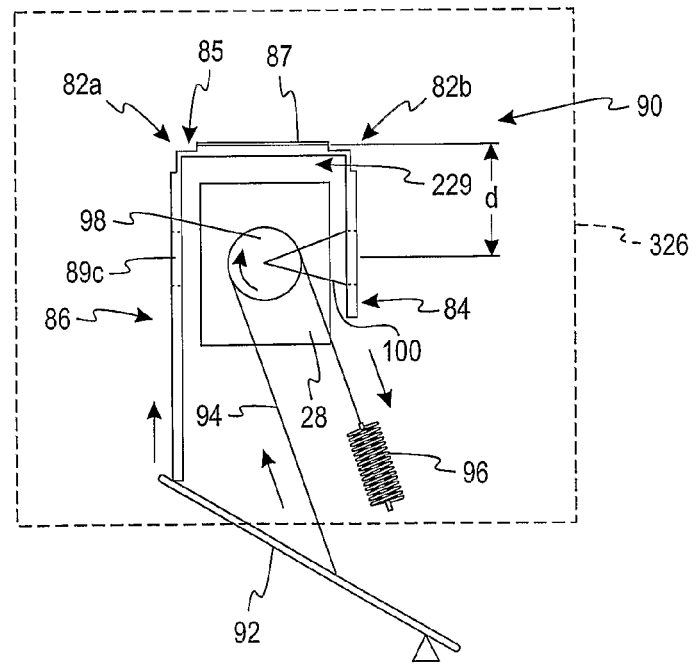
FIG. 10b is a side view of the meter and test strip positioning device after loading a test strip according to one embodiment of the present invention.

Referring now to FIGS. 10a and 10b, a positioning device 90 located within a meter 326 capable of assisting in the folding of the test strip 80 around a read-head 28 is shown. In FIG. 10a the positioning device 90 is shown in a loading position. A receiving member 100 comprises a first receiving area of the positioning device 90 receives the tab end 84 of the test strip 80. An operating lever 92 comprises a second receiving area engages the main end 86 of the test strip 80 and pushes the test strip 80 into the meter as shown in FIG. 10b. A cord 94, which is looped around a pulley 98, is attached to the lever 92 at one end and to a tension spring 96 at the other. The receiving member 100 is attached to and pivots about the pulley 98. Movement of the lever 92 toward the meter 326 permits the tension spring 96 to pull the cord 94, which rotates the receiving member 100 attached to the pulley 98.

In operation, the test strip 80 is inserted tab end 84 first into the positioning device 90 such that the receiving member 100 receives the tab end 84. The alignment aperture 89d of the test strip 80 may be used by the receiving member 100 to engage the test strip 80. The lever 92 engages the main end 86 of the test strip 80. Upon the movement of the lever 92 towards the meter 326, the lever 92 pushes the test strip 80 into the meter 326. At the same time, the movement of the lever 92 toward the meter 326 creates slack in the cord 94 that permits the tension spring 96 to contract. The contraction of the tension spring 96 causes the cord 94 to rotate the pulley 98, which rotates the receiving member 100. The rotation of the receiving member 100 causes the tab end 84 of the test strip 80 to bend at the bend line 82b and the test strip 80 begins to wrap around the read-head 28.

When the lever 92 is moved further, the test strip 80 is further forced into the meter and the receiving member 100 is further rotated. This causes the middle section 85 to begin to wrap around the read-head 28 as well. Thus, the test strip 80 begins a second bend at the bend line 82a. Upon complete actuation of the operating lever 92, the pulley mechanism 98 and the receiving member 100 will have made a complete 180-degree rotation and the test strip 80 will be completely wrapped about the read-head 28, as shown in FIG. 10b.

FIG. 10b shows the top-fill positioning device 90 in its operating position. In the operating position, the middle section 85 and the test element 87 are substantially parallel to the read-head 28 and a spacing 229 has been created between the test element 87 and the read-head 28. The distance of the spacing 229 between the test element 87 and the read-head 28 is predetermined by placing the read-head 28 at a specific position relative to the receiving member 100 when designing the meter 326. The test strip 80 is also folded around the read-head 28, which along with the spacing 229, helps to protect the read-head 28 from contamination by a sample. In this embodiment, an attachment pin (not shown) may be inserted into the alignment aperture 89c to further ensure the stability and placement of the test strip 80.

While the invention is susceptible to various modifications and alternative forms, specific embodiments thereof have been shown by way of example in the drawings and are described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. A system for determining the concentration of an analyte in a fluid sample, the system comprising:
   a test strip including:
      a base having a first portion and a second portion separated by a bend line formed in the base, the bend line traversing the longitudinal axis of the base, the base being adapted to bend about the bend line; and
      a test element disposed on one of the first or second portions of the base, the test element including a reagent adapted to react with the analyte in the fluid sample and to produce a reaction indicative of the concentration of the analyte in the fluid sample; and
   a meter including:
      a read-head adapted to analyze the reaction between the analyte and the reagent; and
      a receiving area adapted to receive the first portion of the base of the test strip,
   wherein the receiving area of the meter receives the first portion of the base of the test strip, the test strip adapted to be bent about the bend line such that the second portion of the test strip is disposed over the read-head, the first portion of the test strip positioning the second portion of the test strip a predetermined distance from the read-head such that a spacing is created between the second portion of the test strip having the test element disposed thereon and the read-head.

2. The system of claim 1 wherein the receiving area is a slot adapted to receive the test strip.

3. The system of claim 1 wherein the receiving area is a first alignment pin.

4. The system of claim 1 wherein the receiving area is a rotating receiving member.

5. The system of claim 1 further including a second receiving area adapted to receive the second portion of the base of the test strip, the second receiving area of the meter receiving the second portion of the base of the test strip when the test strip is bent about the bend line.

6. The system of claim 5 wherein the first receiving area is a first alignment pin and the second receiving area is a second alignment pin.

7. The system of claim 5 wherein the first receiving area contains a positioning device adapted to articulate between a loading position and an operating position, and the second receiving area contains a bridge having an opening.

8. The system of claim 7 wherein the positioning device comprises:
   an arm having a distal end;
   a head attached to the distal end of the arm, the head comprising a platform as its lower boundary and a lip located above and substantially parallel to the platform, wherein the lip and the platform define a moveable slot;
   a channel adapted to receive the arm as it is articulated from the loading position to the operating position; and
   an inlet adapted to receive the platform when the positioning device is in the operating position.

9. The system of claim 5 wherein the first receiving area contains a receiving member adapted to rotate between a loading position and an operating position, and wherein the second receiving area contains an operating lever adapted to articulate between a loading position and an operating position.

10. A method for determining the concentration of an analyte in a fluid sample, the method comprising the acts of:
   providing a test strip including:
      a base having a first portion and a second portion separated by a bend line formed in the base, the bend line traversing the longitudinal axis of the base, the base being adapted to bend about the bend line; and
      a test element disposed on one of the first or second portions of the base, the test element including a reagent adapted to react with the analyte in the fluid sample and to produce a reaction indicative of the concentration of the analyte in the fluid sample;
   providing a meter including:
      a read-head for analyzing the reaction between the analyte and the reagent; and
      a receiving area adapted to receive the first portion of the base;
   receiving the first portion of the test strip in the receiving area; and
   bending the test strip at the bend line to create a spacing between the read-head and the test element, wherein the first receiving area is used to position the second portion of the bent test strip a predetermined distance from the read head.

11. The method of claim 10 further including the act of collecting a fluid sample on the test element disposed on the second portion of the test strip.

12. The method of claim 11 further including the act of determining the concentration of the analyte in the sample by using the read-head to analyze the reaction between the analyte and the reagent.

13. The method of claim 10 wherein the test strip further comprises a double-sided adhesive layer having a capillary space formed therein, the adhesive layer being disposed on the test element opposite the base such that the capillary space extends over the test element, and a lid positioned on the adhesive layer opposite the test element, wherein the lid and the capillary space of the adhesive layer form a capillary channel over the test element.

14. The method of claim 10 wherein the base of the test strip is composed of polyethylene terephthalate.

15. The method of claim 10 wherein the bend line allows the test strip to be bent into a substantially 90-degree angle.

16. The method of claim 10 wherein the width of the test element is approximately the width of the test strip.

17. A test strip for use in the determination of an analyte in a fluid sample, the test strip comprising:
   a base having a first portion and a second portion separated by a bend line formed in the base, the bend line traversing the longitudinal axis of the base, the base being adapted to bend about the bend line;
   a test element being disposed on the base proximate the bend line;
   a double-sided adhesive layer having a capillary space formed therein, the adhesive layer being disposed on the test element opposite the base such that the capillary space extends over the test element; and
   a lid positioned on the adhesive layer opposite the test element, the lid and the capillary space of the adhesive layer forming a capillary channel over the test element.

18. The test strip of claim 17 wherein the lid is composed of polyethylene terephthalate.

19. The test strip of claim 18 wherein the lid has an aperture formed therein for venting the capillary channel.

20. The test strip of claim 17 wherein an inlet to the capillary channel is disposed proximate the bend line.

21. The test strip of claim 17 wherein the test element, adhesive layer, and lid are substantially flush with the bend line.

22. The test strip of claim 21 further comprising a lip that extends from the lid, the lip extending over the bend line and is adapted to direct a sample towards the capillary channel.

23. A test strip for use in the determination of an analyte in a fluid sample, the test strip comprising:
- a base having a first portion and a second portion separated by a bend line formed in the base, the bend line traversing the longitudinal axis of the base, the base being adapted to bend about the bend line;
- a test element being disposed on the base proximate the bend line; and
- at least one alignment aperture that is an aperture extending through the base.

24. A test strip for use in the determination of an analyte in a fluid sample, the test strip comprising:
- a base having a first portion and a second portion separated by a bend line formed in the base, the bend line traversing the longitudinal axis of the base, the base being adapted to bend about the bend line;
- a test element being disposed on the base proximate the bend line; and
- at least one alignment aperture that is an aperture extending at least partially into the base.

25. The test strip of claim 24 wherein the base is composed of polyethylene terephthalate.

26. The test strip of claim 24 wherein the bend line allows the test strip to be bent into a substantially 90-degree angle.

27. The test strip of claim 24 wherein a reagent has been applied to the reaction area of the test element.

28. The test strip of claim 24 wherein the reagent produces a colorimetric reaction.

29. The test strip of claim 24 wherein the width of the test element is approximately the width of the test strip.

30. A test strip for use in the determination of an analyte in a fluid sample, the test strip comprising:
- a base having a first portion, a second portion, and a third portion, the first portion and the second portion separated by a bend line formed in the base, the bend line traversing the longitudinal axis of the base, the base being adapted to bend about the bend line, the third portion separated from the second portion by a second bend line formed in the base, the second bend line traversing the longitudinal axis of the base, the second portion being defined by the first and second bend lines and wherein the bend lines allow the base to be folded;
- a test element being disposed on the base proximate the bend line, the test element located on the second portion between the first and second bend lines; and
- at least one alignment aperture that is an aperture extending through the base.

* * * * *